United States Patent [19]
Black et al.

[11] Patent Number: 5,248,311
[45] Date of Patent: Sep. 28, 1993

[54] FIBER-OPTIC PROBE FOR SOFT-TISSUE LASER SURGERY

[76] Inventors: Michael Black, 560 Trinidad La., Foster City, Calif. 94404; Vladimir Kupershmidt, 3124 Weymouth Ct., Pleasanton, Calif. 94086

[21] Appl. No.: 944,245
[22] Filed: Sep. 14, 1992
[51] Int. Cl.[5] ............................................. A61B 17/36
[52] U.S. Cl. ................................... 606/15; 606/7; 606/11; 606/17; 606/88
[58] Field of Search .................. 606/15, 16, 17, 7; 385/125, 123, 131, 12

[56] References Cited

U.S. PATENT DOCUMENTS

| | | | |
|---|---|---|---|
| 3,641,332 | 2/1972 | Reick et al. | 606/13 |
| 4,519,390 | 5/1985 | Horne | 606/15 |
| 4,630,890 | 12/1986 | Ashkin et al. | 385/123 |
| 4,676,594 | 6/1987 | Presby | 385/123 |
| 4,860,743 | 8/1989 | Abela | 606/15 |
| 4,966,596 | 10/1990 | Kuntz et al. | 606/15 |
| 5,019,075 | 5/1991 | Spears et al. | 606/7 |

*Primary Examiner*—Stephen C. Pellegrino
*Assistant Examiner*—Sonya Harris

[57] ABSTRACT

A fiber-optic probe for soft-tissue laser surgery such as angioplasty comprising a section of an optical fiber having a beam-inlet end (23) and a beam-outlet end (22) and composed of a beam-propagating core (18) and a cladding (19) a part of which is removed in the form of openings (20, 21) through which a portion of the laser beam leaves the fiber-optic probe and is directed laterally to the longitudinal axis 34 of the fiber to the operation site. The intensity distribution of the outgoing beam can be controlled by selecting a required pattern of distribution of the openings.

4 Claims, 2 Drawing Sheets

FIBER-OPTIC PROBE FOR SOFT-TISSUE LASER SURGERY

BACKGROUND

1. Field of the Invention

The present invention relates to medicine, particularly to laser fiber-optic probes for soft tissue surgery, e.g., for angioplasty or endometriosis.

2. Description of Prior Art

At the present time laser techniques find increasing medical applications, in particular in laser surgery on soft tissue, such as laser angioplasty, endometriosis, or tubular reconstructive surgery. For surgical operations, a laser beam should be delivered to the operation site and converted into other forms of energy, such as heat or acoustic energy, which is concentrated within a specific volume. However, operation sites usually are remotely located with respect to the laser-energy source and are often poorly accessible, especially when the operation must be performed inside a blood vessel to remove a plaque which is a localized area of arteriosclerosis. Plastic surgery of diseased blood vessels is called angioplasty. In laser angioplasty an optical fiber is inserted into a blood vessel, moved along the vessel, and used, e.g., for removing plaque from the inner walls of the vessel.

At the present time, however, optical fiber laser angioplasty can be carried out only in relatively short and straight vessels because existing techniques suitable for such operations allow the beam to exit only in a linear path.

In addition, when plaque areas are located asymmetrically, i.e., not opposite to each other on the inner wall of the vessel, simultaneously with the removal of a plaque area, the linearly-directed beam will damage the opposite inner wall.

Thus, in laser angioplasty the laser beam's energy is used inefficiently because the object being treated is located on the wall of a blood vessel while the beam is directed along the vessel. Also the optical fiber is located in a narrow blood vessel and therefore cannot be curved. This is because, in a curved configuration, an optical fiber may preserve its operation characteristics only when the radius of curvature exceeds 3-10. However, the limited space inside the blood vessel does not allow to satisfy this requirement.

Moreover, in a human body none of the blood vessels are ideally straight and some of them have intricate paths, forming V- or U-shaped configurations. In order to treat hard-to-reach areas in such vessels, the laser beam should be able to operate throughout a wide range of angles. The same is true, not only for angioplasty, but also for other types of laser surgery. A more detailed description of optical-fiber laser-surgery techniques is given in "Optical Fibers in Medicine" (SPIE [Society of Photographic Instrumentation Engineers]1990), Volume MS 11, Bellingham, Wash., U.S.A.

In order to solve the above problem, the applicants of the present patent application have developed a surgical-laser endoscopic focusing guide for a laser-fiber optical link. The device comprises a disposable unit which is connected to the end of an optical fiber link. The unit consists of an endoscopic tube, the front end of which contains an optical head with a mirror lens for directing a laser beam emitted from the unit onto the operation site. The lens bends the beam in a lateral direction onto a tissue to be treated. In an embodiment for laser angioplasty, the unit has a firm attachment directly to a buffer layer of the optical fiber link. This ensures flexibility required for operation in narrow and curved vessels and provides firm attachment of the mirror lens to the tube.

However, the optical head used in the above-mentioned device must have a diameter of at least 2-3 mm and a length of at least 4 to 5 mm. Therefore the use of such a device is limited only to angioplasty of large coronary blood vessels, since the optical head cannot be inserted and guided through blood vessels of a small diameter. Furthermore, the surgical endoscopic optical guide has a very limited area of focusing of a laser beam and therefore a nonuniform distribution of laser radiation over the treated surface, which is dangerous for treating narrow blood vessels with extremely thin walls. A mechanism for the attachment of the optical head to an optical fiber link is sufficiently complicated in structure and expensive to manufacture.

OBJECTS OF THE INVENTION

Accordingly, the objects of the present invention are to provide a laser fiber-optic probe for soft-tissue surgery which allows operation in narrow and small blood vessels, which provides a uniform distribution of laser radiation energy over the treated surface, and which is simple in construction and is inexpensive to manufacture.

Other objects and advantages of the invention will become apparent after the consideration of the ensuing description with the attached drawings.

Figure 1:
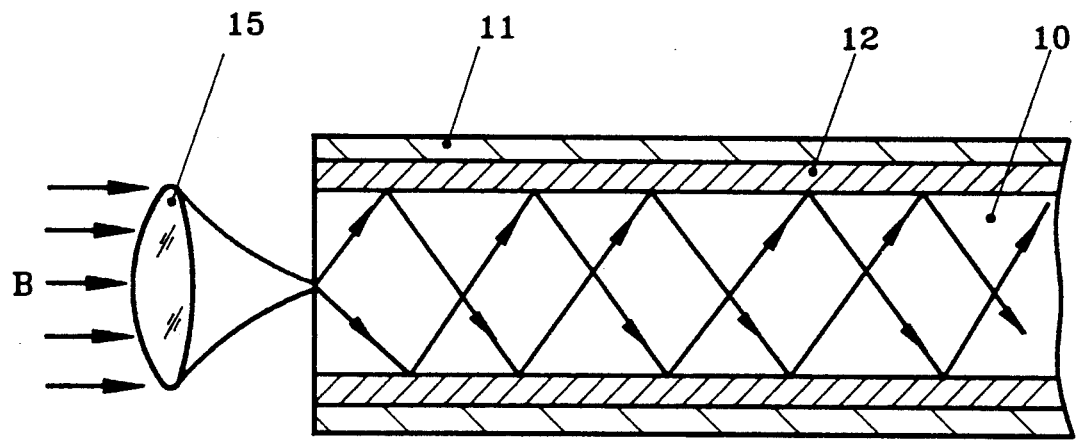
FIG. 1 is a schematic longitudinal sectional view of a conventional optical fiber.

Reference Numerals Used in the Drawings and Description

10—core
11—buffer
12—cladding
13—buffered optical fiber
14—optical fiber
17—buffer
15—focusing element
18—core 7
19—cladding
20, 21—holes
22—output end of the fiber
23—input end of the fiber
24—plaque
26—blood vessel
27—core-cladding interface
28—core
30—cladding
32—one-dimensional perforation
34—optical axis
36—core-cladding interface
38—core-air interface 40—two-dimensional opening
A1, A2, A3—points of reflection
B3-1a, B3-2a, B3-3a—portions of beam B3
B, B3—laser beams
B1, B2—rays
B1a and B2a—rays

FIGS. 1–3—DESCRIPTION OF FIBER-OPTIC PROBE

As shown in FIG. 1, a conventional optical fiber has a core 10 made of a material with a high index of refraction, a cladding 12 which completely surrounds core 10 and is made of a material with an index of refraction lower than that of core 10, and a buffer 11 which covers the entire optical fiber and imparts to it mechanical stability. Buffer 11 may be made of a temperature-resistant polymer such as nylon, Tefzel, silicone, etc. Buffer 11 may be protected by a metallized coating (not shown). A focusing element 15 is installed in front of input end of optical fiber for focusing a laser beam B and for directing it into the fiber.

As a result, while laser beam B propagates through cladded core 10, total internal reflection, i.e., internal reflection without any leakage of the light energy through the side walls of the optical fiber, occurs.

The present invention is based on a principle that openings are made in the cladding or cladding and buffer layers so that a portion of the laser light can be emitted through these openings in the lateral direction of the fiber.

Figure 2:
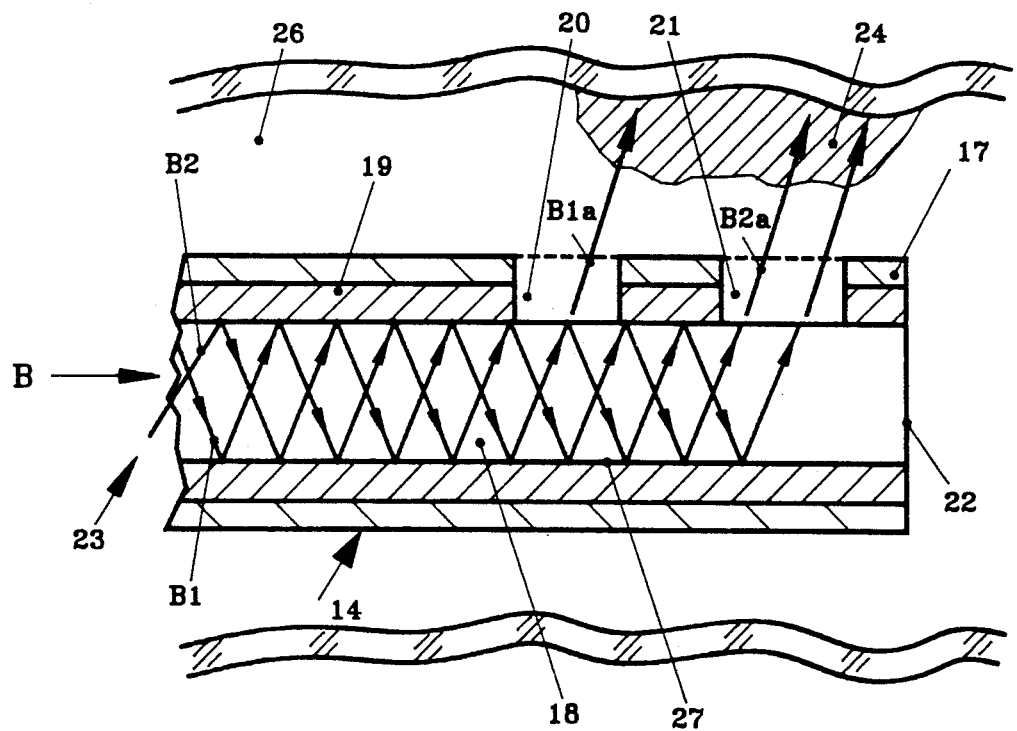
FIG. 2 is a schematic longitudinal sectional view of a fiber-optic probe of the invention inserted into a blood vessel having a plaque.

The invention will be further described in detail with reference to FIGS. 2 and 3. FIG. 2 is a schematic longitudinal sectional view of a fiber-optic probe of the invention inserted into a blood vessel 26 having a plaque 24, and FIG. 3 is a three-dimensional view of a working head of the probe.

As shown in FIG. 2, a fiber-optic probe of the invention has a very simple construction. In fact, it comprises a portion of a conventional optical fiber 14 with appropriate openings in the cladding or cladding and buffer, as described below. Fiber 14, which has a diameter of from 100 μm to 3 mm, consists of a core 18 surrounded by a cladding 19 and buffer 17. Small-diameter holes, such as holes 20 and 21, are formed in cladding 19 on one side of the fiber. Holes 20 and 21 are located near a fiber end 22, e.g., at a distance of 0.5 to 10 mm. Holes 20 and 21 may have a diameter exceeding 10 μm and may be produced by a variety of methods known in the art, such as photolithography, etching, etc.

An end 23 of the fiber opposite to end 22 is an input end through which laser beam B is directed into the fiber-optic probe.

Figure 3:
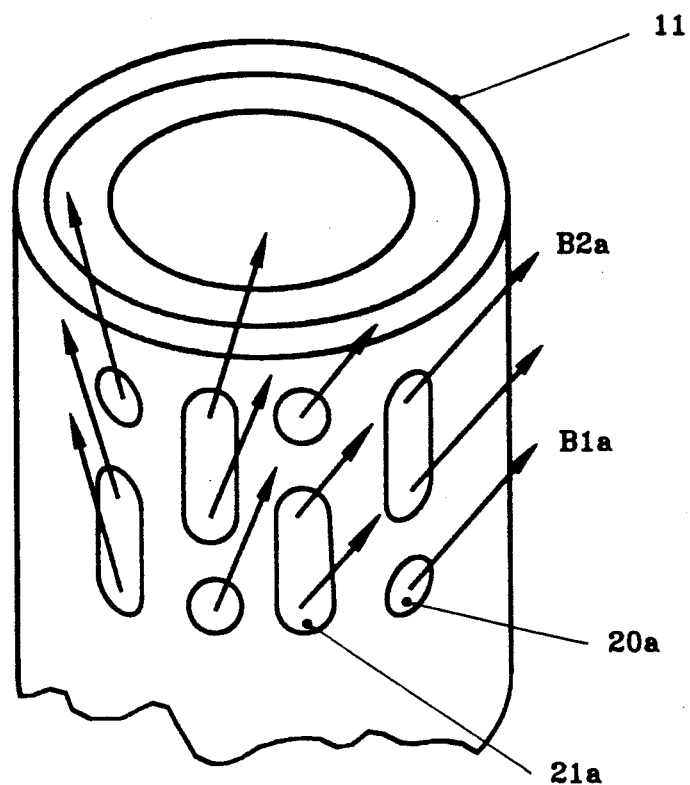
FIG. 3 is a three-dimensional view of a working head of the probe.

Although two holes are shown, for more uniform distribution of the laser beam energy the number of holes in the side wall of the fiber should be much greater than two, as shown in FIG. 3, which is a perspective view of end 22 of the fiber-optic probe. Distribution of light intensity can be controlled by utilizing holes of different size and shape. For example, holes 20a are round and holes 21a are oval. Distribution of the holes may be selected in accordance with specific conditions required for the operation. The holes may be located on both sides or on one side of the fiber-optic probe. The number of the openings and their dimensions may be selected according to a formula shown below in the description of the operation of the fiber-optic probe.

It is recommended that cladding 19 be made of a high-temperature polymer plastic suitable for high-power laser applications and for perforating with the use of the methods mentioned above. Cladding 19 may also be made of glass or silica.

The optical fiber suitable for the invention is produced, e.g., by Fiberguide Industries Co., New Jersey.

FIGS. 1–3. OPERATION

For an angioplastic operation, such as removal of plaque 24 from the inner wall of blood vessel 26, the fiber-optic probe of the invention is inserted into blood vessel 26 so that holes 20 and 21 are aligned with and face plaque 24.

In a conventional manner, a laser beam B which is generated by a laser source (not shown) and, in fact, consists of a plurality of rays B1, B2, etc., only two of which are shown, is directed into core portion 18 of the fiber-optic probe at a predetermined acceptance angle Θ through input end 23. Acceptance angle Θ is an incident angle of laser beam B with respect to the longitudinal axis A of the fiber. Selection of this angle is determined by indices of refraction of core 18 and cladding 19. The sine of this angle is called a "numerical aperture" (NA) of a fiber.

However, due to refraction at laser input end 23 of the fiber, within the material of core 18, laser beam B will propagate at an angle $\phi$ of total internal reflection with respect to the normal to an interface 27 between cladding 20 and core 18.

When rays B1, B2, etc., propagate through core 18, they experience multiple total internal reflection from interface 27 so that when they reach holes 20 and 21, a major fraction of these beams B1a and B2a passes through holes 20 and 21 and impinges plaque 24 at an angle ε. As a result, plaque 24 is ablated under the effect of the laser radiation. At the same time, another, i.e., a minor fraction (i.e., of about 10–15%) of the laser energy of rays B1, B2 is internally reflected into core 18. Thus, rays B1 and B2 continue the multiple-reflection pattern until the beams exit core 18 through end 22.

Thus, the laser energy of beam B will irradiate the operation site, which in the illustrated case is plaque 24, in a uniform manner through multiple holes (FIG. 3) which may be arranged in a required pattern.

Intensity of irradiation of plaque 24 may be controlled by the following three parameters of the system: acceptance angle Θ which is determined by the selection of an appropriate fiber and the value of which for each fiber is unequivocal; the number of the holes; and the diameter of holes in the cladding.

Figure 4:
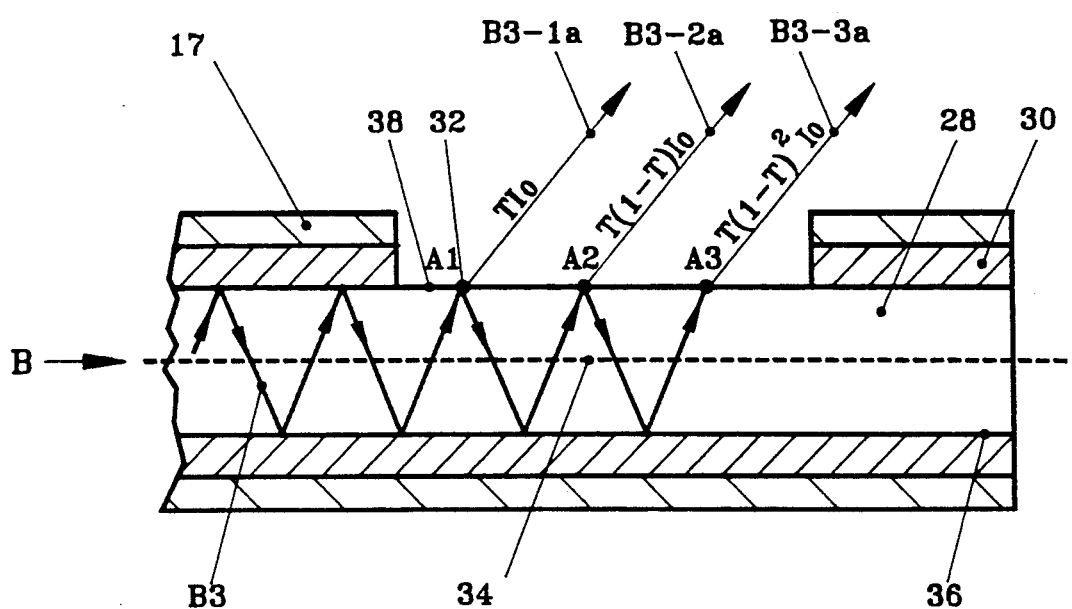
FIG. 4 is a longitudinal sectional view of a perforated portion of the fiber-optic probe illustrating the distribution of beams in the probe.

FIG. 4 is a longitudinal sectional view of a perforated portion of the fiber-optic probe illustrating the distribution of beams in the probe during the operation. The illustrated portion of the probe has a core 28 and a cladding 30 with a linear (one-dimensional) perforation 32 in the direction of an optical axis 34 of the fiber.

As shown in FIG. 4, a laser beam B3, which propagates through the fiber-optic probe, experiences multiple internal reflection from a core-cladding interface 36 and has a laser-energy leakage at each reflection from a core-air interface 38, i.e., from a perforated portion of the probe. For example, beam B3 may have "N" reflections into core 28 and "N" refractions through core-air interface 38. In the case illustrated in FIG. 4, beam B3 has three sequential points of reflection A1, A2, and A3. In each of these points a portion (B3-1a, B3-2a, and B3-3a) of beam B3 is transmitted through interface 38 to the outside, while another portion (B3-1b, B3-2b, and B3-3b) is reflected into core 28 and propagates further in the direction of optical axis 34.

As can be seen from FIG. 4, a beam portion B3-1a, which is refracted at point A1, has intensity of $TI_o$ (where T is the transmittance at core-air interface 38 for all possible propagating modes in a multimode fiber and $I_o$ is the intensity of the laser beam which propagates inside the fiber. A beam portion B3-2a, which is refracted in the second point A2, has the intensity of $T(1-T)I_o$. A beam portion B3-3a has the intensity of $T(1-T)^2I_o$, etc. For N sequential reflections, a beam portion B3-Na will have an intensity of $T(1-T)^NI_o$. By adding all refracted components one can obtain a total intensity I which will leak through core-air interface 38 and which is the function of the fiber parameters.

Let us assume that laser beam B3 which propagates through the portion of the optical fiber, shown in FIG. 4, carries 100% of the energy and that it is required that 90% of this energy be delivered to an operation site (not shown) through the one-dimensional perforation shown in the drawing. Based on this assumption, it is possible to determine the number N of refractions.

Since the distance D between sequential points of refraction A1, A2, ... AN is known and is directly related to the numerical aperture of the fiber NA, it is possible to calculate the length L of one-dimensional perforation 32:

$$L = N \times D.$$

Since in reality perforation 32 is not a one-dimensional slot but rather a two-dimensional opening, it is possible to determine the second dimension Q of opening 32, provided that distribution of the energy over the periphery of the fiber is uniform.

Thus, knowing the quantity of the laser energy which is transmitted through given opening 32, one can determine the total amount of energy that passes through M such openings. Since we know the size of opening 32 and the total amount of energy delivered to the operation site, it is possible to calculate the number M of openings, such as opening 40, for each particular condition from the following equation:

$$\text{Input energy density} \times (L \times Q)M = \text{Output energy}$$

By selecting the number, shape, and distribution of openings, it is possible to completely prevent the leakage of light energy through the end of the probe opposite to the inlet end.

SUMMARY, RAMIFICATIONS, SCOPE

Thus, we have provided a laser fiber-optic probe for angioplasty which allows operation in narrow and curved blood vessels, which provides a uniform distribution of laser radiation energy over the treated surface, and which is simple in construction and is inexpensive to manufacture.

Although the fiber-optic probe has been shown and described in the form of one specific embodiment, its parts, materials, and configurations have been given only as examples, and many other modifications of the fiber-optic probe are possible. For example, the probe may be used not only for angioplasty but also for other types of laser soft-tissue surgery. The openings in the cladding or cladding and buffer may have a distribution pattern and may vary in number, shape, and in size. In this case, the openings will pass through the buffer layer as well. The fiber-optic probe described above may be used not only for laser surgery but also for illumination of the operation site or for any other purpose. The core, cladding, and buffer may be made of materials other than those indicated. E.g., the core may be made of a silver fiber or of a low-OH fiber for infrared applications.

Therefore, the scope of the invention should be determined, not by the example given, but by the appended claims and their legal equivalents.

We claim:

1. A fiber-optic probe for guiding laser beams during removal of plaques from blood vessels, said plaques having a shape, said fiber-optic probe comprising an optical fiber having a beam-inlet end, and a beam-outlet end, said beam-outlet end having specific boundaries corresponding to said shape of said plaques, said optical fiber including:
   a light-propagating core possessing a first refraction index, said light-propagating core having a cylindrical surface;
   a cladding layer completely covering said cylindrical surface of said light-propagating core and having an interface with said light-propagating core, said cladding layer possessing a second refraction index, said first refraction index being higher than said second refraction index, whereby total internal reflection of said laser beams from said interface into the body of said light-propagating core is insured;
   a protective casing completely enclosing said cladding layer; and
   a cluster of openings formed in said protective casing and said cladding layer at the beam outlet end of said probe and exposing said light-propagating core without physical alteration thereof, said openings having non-uniform shapes and sizes, so that said laser beams can exit said light-propagating core through said cluster of openings, said cluster of openings being located within a portion of said beam-outlet end and having a total area large enough to allow all of said laser beams to exit said light-propagating core through said cluster of openings.

2. The fiber-optic probe of claim 1 wherein said openings have shapes selected from the group consisting of circles and ellipsoids.

3. A method of removing plaques from blood vessels by utilizing high-energy optical radiation, said plaques having a shape, said method comprising the steps of:
   determining said shape of said plaques to be removed using a non-invasive-imaging method;
   inserting into a diseased blood vessel an optical probe comprising an optical fiber containing a light-propagating core and a cladding layer, said light-propagating core having a longitudinal axis, said optical fiber having a beam-inlet end, said beam-outlet end comprising a cluster of and having a total area openings formed in said cladding layer to expose said light-propagating core without physical alteration thereof, said openings having non-uniform sizes and shapes corresponding to said shape of said plaques as determined, said total area being large enough to allow all of said high-energy optical radiation to exit said light-propagation core through said cluster of openings;

using said non-emitting end as a guide to move said optical probe through said diseased blood vessel and positioning said beam-outlet end opposite said plaques inside said diseased blood vessel;

directing a beam of said high-energy optical radiation into said beam-inlet end at a predetermined angle which insures total internal reflection of said beam from said cladding into said light-propagating core;

directing said beam through said light-propagating core so that it travels through said light-propagating core by a process of multiple refraction while remaining undisturbed and unaltered; and allowing said beam to completely exit said light-propagating core through said cluster of openings in a direction substantially orthogonal to the longitudinal axis of said light-propagating core and to irradiate said plaques.

4. The method of claim 3 wherein said step of inserting into said diseased blood vessel said optical probe further includes providing said cluster of openings with openings having shapes selected from the group consisting of circles and ellipsoids.

* * * * *